United States Patent
Bourriague-Seve et al.

(10) Patent No.: US 6,939,865 B2
(45) Date of Patent: Sep. 6, 2005

(54) PHARMACEUTICAL DRONEDARONE COMPOSITION FOR PARENTERAL ADMINISTRATION

(75) Inventors: Frédérique Bourriague-Seve, Ferrieres les Verreries (FR); Thierry Breul, Frontignan (FR)

(73) Assignee: Sanofi-Aventis, Paris (FR)

( * ) Notice: Subject to any disclaimer, the term of this patent is extended or adjusted under 35 U.S.C. 154(b) by 82 days.

(21) Appl. No.: 10/450,320

(22) PCT Filed: Dec. 10, 2001

(86) PCT No.: PCT/FR01/03903

§ 371 (c)(1),
(2), (4) Date: Jun. 10, 2003

(87) PCT Pub. No.: WO02/47660

PCT Pub. Date: Jun. 20, 2002

(65) Prior Publication Data

US 2004/0044070 A1 Mar. 4, 2004

(30) Foreign Application Priority Data

Dec. 11, 2000 (FR) .............................. 00 16071

(51) Int. Cl.$^7$ .......................... A61K 31/34; A61K 31/70
(52) U.S. Cl. ......................................... 514/58; 514/469
(58) Field of Search ..................................... 514/58, 469

(56) References Cited

U.S. PATENT DOCUMENTS 5,985,915 A    11/1999   Frangin et al.  .............. 514/469

OTHER PUBLICATIONS

Verduyn, S.C.; Vos, Ma; Leunissen, H.D.; "Evaluation of the acute electrophysiologic effects of intraveneous Dronedarone . . . "; Journal of Cardiovascular Pharmacology, vol. 33, no. 2, 1999, pp 212–222; XP001024499, p 213, col. 2, lines 44–62.

Manning, A; Thisse, V.; Hodeige, D.; "SR33589, a new amiadarone–like antiarrhythmic agent . . . "; Journal of Cardiovascular Pharmacology, vol. 25, no. 2, 1995, pp 252–261; XP001024497, p 253, col. 2, lines 1–18.

*Primary Examiner*—Elli Peselev
(74) *Attorney, Agent, or Firm*—M. Alexander; Kelly Bender

(57) ABSTRACT

A subject-matter of the invention is a pharmaceutical composition for parenteral administration, characterized in that it comprises: dronedarone or one of its pharmaceutically acceptable salts as active principle; a physiologically acceptable buffer solution capable of maintaining the pH of the composition between 3 and 5; a physiologically acceptable water-soluble β-cyclodextrin derivative.

38 Claims, No Drawings

PHARMACEUTICAL DRONEDARONE COMPOSITION FOR PARENTERAL ADMINISTRATION

This application is a 35 U.S.C. § 371 application of PCT International Application No. PCT/FR01/03903 filed Dec. 10, 2001.

The present invention relates generally to a novel pharmaceutical composition comprising, as active principle, a benzoylbenzofuran derivative.

In particular, the invention relates to a pharmaceutical composition for parenteral administration comprising, as active principle, 2-butyl-3-(4-[[3-(dibutylamino)propoxy]] benzoyl)-5-(methanesulphonamido)benzofuran, also known as dronedarone, or one of its pharmaceutically acceptable salts, preferably its hydrochloride.

This (methanesulphonamido)benzofuran derivative and its pharmaceutically acceptable salts have been disclosed in Patent EP 0 471 609, along with its therapeutic applications.

This compound has been shown to be particularly advantageous in the cardiovascular field, in particular as antiarrhythmic agent.

Dronedarone, in the form of its hydrochloride, exhibits a limited solubility in an aqueous medium: at ambient temperature, it is 0.5 mg/ml at pH=4.85. In the pH range from 1.5 to 5, this solubility is virtually constant and then becomes virtually negligible at pH values of greater than 5.5.

However, the solubility of dronedarone hydrochloride is increased in the presence of a mono-sodium phosphate buffer ($NaH_2PO_4$): at ambient temperature, it varies from 2 mg/ml to 2.25 mg/ml in the pH range from 1.5 to 5, whereas it suddenly decreases to become virtually zero at pH=5.5.

Tests carried out on rats lasting several days with an aqueous formulation comprising 1.065 mg/ml of dronedarone hydrochloride in the presence of a phosphate buffer have shown, however, poor local tolerance of this composition, in contrast to an identical formulation devoid of this hydrochloride.

Moreover, dronedarone has powerful ionic surfactant properties leading, in aqueous solution, to a marked decrease in the surface tension. This surfactant nature moreover proves to be as powerful in the presence as in the absence of a phosphate buffer and can be held as being partially responsible for a self-aggregation of dronedarone molecules in aqueous solution. In fact, this supramolecular organization in solution is due to the formation of dimers positioned head to tail and stacked in superimposed layers. These dimers, when they are administered by injection, lead to rupturing of the cell membrane and, consequently, to the appearance of inflammation at the injection site. Generally, these surfactant properties of dronedarone can be regarded as responsible for poor tolerance of the composition in which they are present.

It has been reported, in Patent U.S. Pat. No. 4,727,064, that aqueous solutions of cyclodextrin derivatives, in particular hydroxypropyl-β-cyclodextrin, are capable of increasing the solubility of medicinal active principles, these solutions of cyclodextrin derivatives not causing local irritation. However, no indication appears therein on the subject of the local tolerance of such solutions of β-cyclodextrin derivatives also comprising a medicinal active principle.

In the context of the invention, it has been hypothesized that cyclodextrin derivatives present in an aqueous dronedarone formulation, for example in the form of its hydrochloride, might improve the tolerance of this active principle when administered parenterally.

From this viewpoint, tests were carried out on rats lasting several days with an aqueous formulation comprising 1.065 mg/ml of dronedarone hydrochloride in the presence of a cyclodextrin derivative, in this instance hydroxypropyl-β-cyclodextrin. However, the administration of such a composition showed a marked intolerance at the injection site, whereas an identical formulation, devoid however of dronedarone hydrochloride, proved to be well tolerated.

The search for an injectable dronedarone formulation, dronedarone preferably being in the form of one of its pharmaceutically acceptable salts, such as its hydrochloride, which is both sufficiently concentrated for therapeutic use and devoid of the disadvantages reported above consequently is of indisputable interest.

In point of fact, it has now been discovered, surprisingly, according to the invention that it is possible to have available aqueous dronedarone solutions, dronedarone being in particular in the form of its hydrochloride, which are both concentrated and possessed of acceptable tolerance when they are administered.

In fact, it can be demonstrated that β-cyclodextrin derivatives, when they are used in combination with an appropriate buffer medium, are capable of increasing the solubility of dronedarone or of its pharmaceutically acceptable salts and of preventing their self-aggregation.

Consequently, the invention relates to a pharmaceutical composition for parenteral administration comprising:
  dronedarone or one of its pharmaceutically acceptable salts as active principle,
  a physiologically acceptable buffer solution capable of maintaining the pH of the composition between 3 and 5,
  a physiologically acceptable water-soluble β-cyclodextrin derivative.

In the continuation of the description and in the claims, and unless otherwise indicated, the percentages of the various constituents forming the compositions of the invention, namely the active principle, the buffer medium, the β-cyclodextrin derivative or any other additional ingredient, all express proportions by weight, namely percentages by weight, of the final composition.

Dronedarone, preferably in the form of one of its pharmaceutically acceptable salts, for example the hydrochloride, is present in the compositions of the invention in a proportion of 0.01% to 4%, for example in a proportion of 0.1% to 0.8%. However, preferred compositions comprise from 0.4% to 0.8% of dronedarone or of one of its pharmaceutically acceptable salts.

Generally, the buffer solution is chosen from physiologically acceptable aqueous solutions capable both of dissolving the active principle and of maintaining the pH of the compositions between 3 and 5.

Thus, buffer solutions which can be used in the context of the invention may be, for example, aqueous solutions comprising a buffer system chosen from the following:
  acetic acid/alkali metal acetate,
  fumaric acid/alkali metal fumarate,
  succinic acid/alkali metal succinate,
  citric acid/alkali metal citrate,
  tartaric acid/alkali metal tartrate,
  lactic acid/alkali metal lactate,
  maleic acid/alkali metal maleate,
  methanesulphonic acid/alkali metal methanesulphonate,
  monoalkali metal phosphate,
the alkali metal in each of the above salts being, for example, sodium or potassium.

Use is preferably made, as buffer, of a monoalkali metal phosphate, for example monosodium phosphate or monopotassium phosphate. This buffer is capable of maintaining the pH of the composition at 4.5, an increase in the pH from this value leading to a severe decrease in the aqueous solubility of dronedarone, in particular of its hydrochloride.

In the majority of cases, the ionic strength of the buffer solution will be between 0.005 molar and 0.5 molar, preferably between 0.01 and 0.2 molar, for example from 0.05 to 0.15 molar. Beyond 0.5 molar, there is a risk of the concentration of salts in the medium disturbing the stability of the compositions of the invention and leading to the formulations becoming hypertonic, whereas, at a concentration of less than 0.005 molar, the buffer effect becomes non-existent.

Mention may be made, by way of example, of 0.05 to 0.15 molar aqueous buffer solutions of monoalkali metal phosphate, for example monosodium phosphate or monopotassium phosphate.

With regard to the water-soluble β-cyclodextrin derivative, it is chosen from physiologically acceptable compounds of this type, this derivative generally being more soluble in water than β-cyclodextrin itself. Furthermore, the latter has proved to be unusable because of its low aqueous solubility and because of its toxicity.

Mention may be made, as examples of β-cyclodextrin derivatives which can be used in the compositions of the invention, of the sulphobutyl ether derivative of β-cyclodextrin, dimethyl-β-cyclodextrin, trimethyl-β-cyclodextrin, and their mixtures. However, it is preferable to use hydroxypropyl-β-cyclodextrin.

Generally, the β-cyclodextrin derivative is incorporated in the parenteral compositions in a proportion of 0.5% to 50%, preferably of 1% to 10%, for example 5%, and of 5 to 20 times the weight of dronedarone or of one of its pharmaceutically acceptable salts, preferably of 10 to 15 times this weight and more particularly of 12 to 13 times this weight.

As indicated above, the above β-cyclodextrin derivatives, when they are used in combination with an appropriate buffer, for example a phosphate buffer, in the compositions of the invention, make it possible in particular to increase the aqueous solubility of dronedarone or of its pharmaceutically acceptable salts. In the case, for example, of dronedarone hydrochloride, the solubility can be increased under these conditions up to approximately 6.5 mg/ml in the presence of a 100 mmolar phosphate buffer and of 5% of hydroxypropyl-β-cyclodextrin.

In addition, these β-cyclodextrin derivatives, in particular hydroxypropyl-β-cyclodextrin, have proved to be capable of preventing the self-association of molecules of dronedarone or of its pharmaceutically acceptable salts by formation of an encapsulation complex of this active principle. This molecular encapsulation complex subsequently proved to be capable of passing through the cell membrane while keeping it intact and, consequently, of overcoming the problems of local intolerance demonstrated with compositions comprising either an appropriate buffer or a β-cyclodextrin derivative.

If necessary, the compositions of the invention can comprise one or more additional ingredients, in particular a preservative or protective agent, such as a bactericide, or a compound which makes it possible to maintain the isotonicity of the composition, such as mannitol.

The compositions of the invention thus formed are characterized by high stability, which makes it possible both to store them in a lasting fashion and to use them effectively for administration by injection.

The pharmaceutical compositions of the invention can be obtained conventionally by heating, to a temperature of 50° C. to 60° C., preferably to 55° C., an aqueous medium formed of the appropriate buffer system, of the soluble β-cyclodextrin derivative and of the optional additional excipients, and by then introducing therein, at this temperature, the active principle.

The characteristics and advantages of the compositions according to the invention will become apparent in the light of the description below starting from compositions given by way of examples.

I. Local Tolerance in Animals

Tests were carried out for the purpose of evaluating the local tolerance of various aqueous compositions comprising dronedarone hydrochloride or only the corresponding vehicle as placebo.

To this end, a dose of one the aqueous compositions hereinbelow was administered daily for 5 days via the intravenous route to batches of 5 male rats. The injection was made in the caudal vein, preferably in the distal region, then in the median region and finally in the proximal region. The animals were then sacrificed on the 8th day and the tails were removed for the purpose of possible microscopic examination.

The following results were obtained:
a) Compositions comprising 0.1% of dronedarone base
   Dose administered: 5 ml/kg, i.e. 5 mg/kg/day
   Compositions tested

| INGREDIENTS | COMPOSITION (in mg) | | | | | |
| --- | --- | --- | --- | --- | --- | --- |
|  | A | B | C | D | E | F |
| Dronedarone hydrochloride (corresponding to 1 mg of dronedarone base) | 1.065 | — | 1.065 | — | 1.065 | — |
| Hydroxypropyl-β-cyclodextrin | 50 | 50 | 50 | 50 | — | — |
| Anhydrous monosodium phosphate | 12 | 12 | — | — | 12 | 12 |
| Nonpyrogenic mannitol | 8 | 8 | 45 | 45 | 20 | 20 |

These ingredients are added to the amount of water sufficient to produce a volume of 1 ml.

Compositions A, B, E and F have a pH of 4.5 and compositions C and D a pH of between 4.5 and 6.5.

1) Composition A (or composition comprising a β-cyclodextrin derivative and a phosphate buffer) No local clinical sign was recorded.

The local tolerance of this formulation can be regarded as very good.

2) Compositions B, D and F (or placebo compositions) No local clinical sign was recorded.

3) Composition C (or composition comprising a β-cyclodextrin derivative but no phosphate buffer) After a single injection, the tails of all the animals exhibited local red patches and felt hard. Starting from the second injection, the following injections proved to be distressing and had to be carried out in the median segment and then the proximal segment (base) of the tail.

Due to the state of the tail, it was no longer possible subsequently to carry out injections. Thus, 2 animals were able to receive only 3 injections, 2 others received only 4 injections while only one was able to be treated for the 5 days. On the 5th day, the tails of 4 animals appeared black (probable necrosis).

Local intolerance of this composition is regarded as severe.

4) Composition E (or composition comprising a phosphate buffer but no β-cyclodextrin derivative) After 1 or 3 injections, the tails of the animals exhibited local red patches over their entire length. On the 4th day, 2 animals had to be injected in the median segment (and no longer in the distal segment). On the 5th day, the technical difficulties due to the poor condition of the tails prevented the treatment of 4 animals and the tails of all the animals were hard.

Local intolerance to this formulation is regarded as marked.

In conclusion, these combined results clearly show that, among compositions comprising dronedarone hydrochloride, only the formulation involving both a buffer and a β-cyclodextrin derivative showed satisfactory local tolerance.

b) Compositions comprising 0.4% of dronedarone base
Dose administered: 2 ml/kg, i.e. 2 mg/kg/day
Compositions tested

| INGREDIENTS | COMPOSITION (in mg) | | | |
|---|---|---|---|---|
| | G | H | I | J |
| Dronedarone hydrochloride (corresponding to 4 mg of dronedarone base) | 4.260 | — | 4.260 | — |
| Hydroxypropyl-β-cyclodextrin | 50 | 50 | — | — |
| Mixture of methylated derivatives of β-cyclodextrin | — | — | 50 | 50 |
| Anhydrous monosodium phosphate | 12 | 12 | 12 | 12 |
| Nonpyrogenic mannitol | 8 | 8 | 8 | 8 |

These ingredients are added to the amount of water sufficient to produce a volume of 1 ml.

The four compositions have a pH of 4.5.

1) Compositions G and I (or compositions comprising a β-cyclodextrin derivative and a phosphate buffer)
No local clinical sign was recorded.
2) Compositions H and J (or placebo compositions)
No local clinical sign was recorded.

The local tolerance of these formulations can be regarded as very good and equivalent.

These results again show the excellent local tolerance of the compositions comprising dronedarone hydrochloride when these compositions include both an appropriate buffer and a β-cyclodextrin derivative.

II. Local Tolerance in Man

Comparative tests were carried out for the purpose of evaluating the local tolerance of two dronedarone hydrochloride formulations, one comprising a phosphate buffer but no β-cyclodextrin derivative, in this instance Composition E, and the other including these two compounds, namely:

| INGREDIENTS | COMPOSITION K (in mg) |
|---|---|
| Dronedarone hydrochloride (corresponding to 4 mg of dronedarone base) | 4.26 |
| Nonpyrogenic mannitol | 8.0 |
| Hydroxypropyl-β-cyclodextrin | 50.0 |
| Monosodium phosphate dihydrate | 15.6 |

These ingredients are added to the amount of water sufficient to produce a volume of 1 ml.

A) In a first series of tests, 28 healthy male subjects were used, divided into 7 groups of 4 subjects:

3 subjects in each group received, from Composition E administered by perfusion into the antecubital vein, a dose of dronedarone hydrochloride corresponding to 5, 10, 20 or 40 mg of dronedarone base, this taking 30 minutes, or a dose of dronedarone hydrochloride corresponding to 40, 60 or 80 mg of dronedarone base, this taking 60 minutes, 1 subject per group having received the placebo, also by perfusion.

This Composition E was used after diluting in a 5% dextrose solution, so as to obtain, for each of the tests, a concentration of active principle of 0.333 mg/ml. Consequently, the perfusion volume and the rate of administration per minute changed for each dose tested.

Following these perfusions, 2 subjects who had received their dose over 30 minutes exhibited phlebitis, which disappeared, leaving behind a hardening of the vein still present after 8 days.

Likewise, 3 subjects who had received their dose over 60 minutes exhibited chemically-induced phlebitis. The latter disappeared but left a hardening of the vein still present after 8 days.

None of the subjects who had received the placebo displayed a reaction at the site of perfusion.

B) In a second series of tests, 32 healthy male subjects were used, divided into 5 groups:

3 subjects in 2 groups received, from Composition K administered by perfusion in the antecubital vein, a dose of dronedarone hydrochloride corresponding to 10 or 20 mg of dronedarone base, this taking 30 minutes, 1 subject per group having received the placebo, also by perfusion.

6 subjects in 3 groups received, from Composition K administered by perfusion in the antecubital vein, a dose of dronedarone hydrochloride corresponding to 40, 60 or 80 mg of dronedarone base, this taking 30 minutes, 2 subjects per group having received the placebo, also by perfusion.

This Composition K was used after diluting in a 5% dextrose solution. In addition, the perfusion volume was set at 120 ml and the rate of administration at 4 ml/minute.

Consequently, the concentration of dronedarone hydrochloride increased in the perfusion fluid according to the dose of active principle to be administered, changing from 0.083 mg/ml for a dose of 10 mg to 0.666 mg/ml for a dose of 80 mg.

Following these perfusions, the local tolerance appeared to be better than with Composition E, since no phlebitis or chemically-induced phlebitis was recorded at any of the doses tested.

In comparison with Composition E, the results recorded with Composition K are particularly noteworthy at the doses of 40, 60 and 80 mg since the duration of perfusion was shorter (30 minutes instead of 60 minutes for Composition E) and the concentration of the perfusion fluid administered was higher.

In fact, at the dose of 80 mg, the concentration of dronedarone hydrochloride in the perfused Composition K was 0.666 mg/ml instead of 0.333 mg/ml [lacuna] the case of Composition E.

These results confirm with regard to human beings the very good tolerance of the compositions comprising dronedarone hydrochloride, an appropriate buffer and a β-cyclodextrin derivative in comparison with the analogous compositions devoid of a buffer.

The following nonlimiting examples illustrate the invention.

EXAMPLE 1

Injectable Dronedarone Hydrochloride Composition

An injectable pharmaceutical composition corresponding to the following formulation:

| | |
|---|---|
| Dronedarone hydrochloride (corresponding to 4 mg of dronedarone base) | 4.26 mg |
| Hydroxypropyl-β-cyclodextrin | 50.00 mg |

| -continued | |
|---|---|
| Monosodium phosphate dihydrate | 15.60 mg |
| Mannitol | 8.00 mg |

Water (for Injections) amount sufficient for 1 ml is prepared by application of the process described hereinbelow.

50 mg of hydroxypropyl-β-cyclodextrin, 15.6 mg of monosodium phosphate dihydrate and 8 mg of mannitol are dissolved in 75% of the total water for injections. The solution obtained is heated to 55° C. and then, with magnetic stirring, 4.26 mg of dronedarone hydrochloride are introduced. Magnetic stirring is continued for 30 minutes and then the solution is made up to 100% of the final volume with water for injections. The dronedarone hydrochloride solution is filtered through a membrane with a porosity of 0.22 mm and the clarity of this solution, the pH and the osmolality are checked.

The following results were obtained: Turbidity: 1.1 NTU (nephelometric turbidity unit)
pH: 4.5
Osmolality: 311 mosmol/kg The solution thus obtained is clear and isotonic. It can be brought in an autoclave to 121° C. for 35 minutes. It is stable for 6 months at 5° C., 25° C. and 40° C. and can be diluted in a 5% glucose and 0.9% sodium chloride solution.

EXAMPLES 2 TO 4

By following the same method as in Example 1, the following compositions were prepared:

| Ex. 2 | |
|---|---|
| Dronedarone hydrochloride (corresponding to 4 mg of dronedarone base) | 4.26 mg |
| Hydroxypropyl-β-cyclodextrin | 50.00 mg |
| Anhydrous monosodium phosphate | 12.00 mg |
| Mannitol | 8.00 mg |
| Water (for Injections) | amount sufficient for 1 ml |

| Ex. 3 | |
|---|---|
| Dronedarone hydrochloride (corresponding to 1 mg of dronedarone base) | 1.065 mg |
| Hydroxypropyl-β-cyclodextrin | 50.00 mg |
| Anhydrous monosodium phosphate | 12.00 mg |
| Mannitol | 8.00 mg |
| Water (for Injections) | amount sufficient for 1 ml |

| Ex. 4 | |
|---|---|
| Dronedarone hydrochloride (corresponding to 4 mg of dronedarone base) | 4.26 mg |
| Mixture of methylated derivatives of β-cyclodextrin | 50.00 mg |
| Mannitol | 8.00 mg |

| -continued | |
|---|---|
| Ex. 4 | |
| Water (for Injections) | amount sufficient for 1 ml |

EXAMPLE 5

Dosage Unit for Injectable Administration of Dronedarone Hydrochloride

A glass vial with a total volume of 3 ml, comprising 1 ml of a dronedarone hydrochloride composition as prepared in Example 1, is sterilized in an autoclave at 121° C. for 35 minutes.

The vial is then sealed under aseptic conditions, so as to constitute a dosage unit comprising 4.26 mg of dronedarone hydrochloride, equivalent to 0.4% of dronedarone base.

What is claimed is:

1. A pharmaceutical composition for parenteral administration comprising:
    dronedarone or one of its pharmaceutically acceptable salts as active principle,
    a physiologically acceptable buffer solution capable of maintaining the pH of the composition between 3 and 5,
    a physiologically acceptable water-soluble β-cyclodextrin derivative.

2. A pharmaceutical composition according to claim 1 comprising from 0.01% to 4% of active principle.

3. A pharmaceutical composition according to claim 2 comprising from 0.4 to 0.8% of active principle.

4. A pharmaceutical composition according to claim 3 wherein the buffer solution is an aqueous solution comprising a buffer system chosen from the following:
    acetic acid/alkali metal acetate,
    fumaric acid/alkali metal fumarate,
    succinic acid/alkali metal succinate,
    citric acid/alkali metal citrate,
    tartaric acid/alkali metal tartrate,
    lactic acid/alkali metal lactate,
    maleic acid/alkali metal maleate,
    methanesulphonic acid/alkali metal methanesulphonate, or
    monoalkali metal phosphate.

5. A pharmaceutical composition according to claim 4 wherein the buffer system is a monoalkali metal phosphate.

6. A pharmaceutical composition according to claim 5 wherein the monoalkali metal phosphate buffer solution maintains the pH at 4.5.

7. A pharmaceutical composition according to claim 6 wherein the ionic strength of the buffer solution is between 0.005 molar and 0.5 molar.

8. A pharmaceutical composition according to claim 7 wherein the ionic strength of the buffer solution is between 0.01 molar and 0.2 molar.

9. A pharmaceutical composition according to claim 8 wherein the ionic strength of the buffer solution is between 0.05 and 0.15 molar.

10. A pharmaceutical composition according to claim 9 wherein the buffer solution is a 0.05 to 0.15 molar aqueous solution of monoalkali metal phosphate.

11. A pharmaceutical composition according to claim 10, wherein the alkali metal is sodium or potassium.

12. A pharmaceutical composition according to claim 11 wherein the water-soluble β-cyclodextrin derivative is chosen from hydroxypropyl-β-cyclodextrin, the sulphobutyl ether derivative of β-cyclodextrin, dimethyl-β-cyclodextrin, trimethyl-β-cyclodextrin, and their mixtures.

13. A pharmaceutical composition according to claim 12 wherein the water-soluble β-cyclodextrin derivative is hydroxypropyl-β-cyclodextrin.

14. A pharmaceutical composition according to claim 13 wherein the hydroxypropyl-β-cyclodextrin is present in a proportion of 0.5 to 50%.

15. A pharmaceutical composition according to claim 14 wherein the hydroxypropyl-β-cyclodextrin is present in a proportion of 5 to 20 times the weight of dronedarone or of one of its pharmaceutically acceptable salts.

16. A pharmaceutical composition according to claim 15 wherein the hydroxypropyl-β-cyclodextrin is present in a proportion of 12 to 13 times the weight of dronedarone or of one of its pharmaceutically acceptable salts.

17. A pharmaceutical composition according to claim 16 additionally comprising a preservative.

18. A pharmaceutical composition according to claim 16 additionally comprising a compound which makes it possible to maintain the isotonicity.

19. A pharmaceutical composition according to claim 1 wherein the active principle is dronedarone hydrochloride.

20. A pharmaceutical composition according to claim 1 wherein the buffer solution is an aqueous solution comprising a buffer system chosen from the following:

acetic acid/alkali metal acetate,
   fumaric acid/alkali metal fumarate,
   succinic acid/alkali metal succinate,
   citric acid/alkali metal citrate,
   tartaric acid/alkali metal tartrate,
   lactic acid/alkali metal lactate,
   maleic acid/alkali metal maleate,
   methanesulphonic acid/alkali metal methanesulphonate, or
   monoalkali metal phosphate.

21. A pharmaceutical composition according to claim 11 wherein the water-soluble β-cyclodextrin derivative is chosen from hydroxypropyl-β-cyclodextrin, the sulphobutyl ether derivative of β-cyclodextrin, dimethyl-β-cyclodextrin, trimethyl-β-cyclodextrin, and their mixtures.

22. A pharmaceutical composition according to claim 1 wherein the water-soluble β-cyclodextrin derivative is hydroxypropyl-β-cyclodextrin.

23. A pharmaceutical composition according to claim 1 additionally comprising a preservative.

24. A pharmaceutical composition according to claim 1 additionally comprising a compound which makes it possible to maintain the isotonicity.

25. A pharmaceutical composition according to claim 3 wherein the active principle is dronedarone hydrochloride.

26. A pharmaceutical composition according to claim 4 wherein the ionic strength of the buffer solution is between 0.005 molar and 0.5 molar.

27. A pharmaceutical composition according to claim 4 wherein the buffer solution is a 0.05 to 0.15 molar aqueous solution of monoalkali metal phosphate.

28. A pharmaceutical composition according to claim 5, wherein the alkali metal is sodium or potassium.

29. A pharmaceutical composition according to claim 11 wherein the active principle is dronedarone hydrochloride.

30. A pharmaceutical composition according to claim 13 wherein the active principle is dronedarone hydrochloride.

31. A pharmaceutical composition according to claim 14 wherein the active principle is dronedarone hydrochloride.

32. A pharmaceutical composition according to claim 16 wherein the active principle is dronedarone hydrochloride.

33. A pharmaceutical composition according to claim 20 wherein the water-soluble β-cyclodextrin derivative is chosen from hydroxypropyl-β-cyclodextrin, the sulphobutyl ether derivative of β-cyclodextrin, dimethyl-β-cyclodextrin, trimethyl-β-cyclodextrin, and their mixtures.

34. A pharmaceutical composition according to claim 22 wherein the hydroxypropyl-β-cyclodextrin is present in a proportion of 0.5 to 50%.

35. A pharmaceutical composition according to claim 1 comprising:

4.26 mg of dronedarone hydrochloride;
   50.00 mg of hydroxypropyl-β-cyclodextrin;
   15.60 mg of monosodium phosphate dihydrate; and
   8.00 mg of mannitol.

36. A pharmaceutical composition according to claim 1 comprising:

4.26 mg of dronedarone hydrochloride;
   50.00 mg of hydroxypropyl-β-cyclodextrin;
   12.00 mg of anhydrous monosodium phosphate; and
   8.00 mg of mannitol.

37. A pharmaceutical composition according to claim 1 comprising:

1.065 mg of dronedarone hydrochloride;
   50.00 mg of hydroxypropyl-β-cyclodextrin;
   12.00 mg of anhydrous monosodium phosphate; and
   8.00 mg of mannitol.

38. A pharmaceutical composition according to claim 1 additionally comprising a bactericide.

* * * * *